(12) United States Patent
Dalko et al.

(10) Patent No.: US 7,182,949 B2
(45) Date of Patent: Feb. 27, 2007

(54) COMPOSITION COMPRISING VITAMIN C PREPARED DURING APPLICATION, USE OF ENZYMES FOR FORMING VITAMIN C FOR TOPICAL USE, AND A COSMETIC TREATMENT METHOD

(75) Inventors: Maria Dalko, Gif sur Yvette (FR); Rui Pereira, La Riche (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 10/076,418

(22) Filed: Feb. 19, 2002

(65) Prior Publication Data

US 2002/0165271 A1    Nov. 7, 2002

(30) Foreign Application Priority Data

Feb. 19, 2001    (FR)    ................... 01 022234

(51) Int. Cl.
| | |
|---|---|
| A61K 9/00 | (2006.01) |
| A61K 9/10 | (2006.01) |
| A61K 9/48 | (2006.01) |
| A61K 9/50 | (2006.01) |
| A61K 38/44 | (2006.01) |
| A61K 36/00 | (2006.01) |
| A61K 35/00 | (2006.01) |

(52) U.S. Cl. .................. 424/400; 424/401; 424/78.02; 424/94.4; 424/725; 424/780

(58) Field of Classification Search ................ 424/400, 424/49, 451, 489, 78.02, 520, 94.4, 725, 424/780, 401
See application file for complete search history.

(56) References Cited

U.S. PATENT DOCUMENTS

| 4,935,359 | A | | 6/1990 | Yin et al. |
|---|---|---|---|---|
| 5,122,536 | A | * | 6/1992 | Perricone |
| 5,607,921 | A | | 3/1997 | Bernard et al. |
| 5,788,972 | A | | 8/1998 | De Salvert et al. |
| 5,945,447 | A | * | 8/1999 | Fallick |
| 6,060,512 | A | | 5/2000 | Yu et al. |
| 6,153,205 | A | | 11/2000 | Boussouira et al. |
| 6,239,174 | B1 | | 5/2001 | Afriat et al. |
| 6,337,066 | B1 | | 1/2002 | Jacquier |

2002/0012979 A1 *    1/2002    Berry et al.

FOREIGN PATENT DOCUMENTS

| EP | 0 476 442 A2 | 3/1992 |
|---|---|---|
| EP | 0 487 404 A1 | 5/1992 |
| EP | 0 487 404 B1 | 5/1992 |
| EP | 0 710 478 A1 | 5/1996 |
| EP | 0 710 478 B1 | 5/1996 |
| FR | 2680466 * | 2/1993 |
| GB | 763055 A | 12/1956 |
| GB | 2 008 116 A | 5/1979 |
| JP | 54-145283 | 11/1979 |
| JP | 61-500201 | 2/1986 |
| JP | 64-34293 | 2/1989 |
| JP | 6-46870 | 2/1994 |
| JP | 7-96166 | 4/1995 |
| JP | 8-133925 | 5/1996 |
| WO | 85/01745 A1 | 4/1985 |
| WO | 93/19192 A1 | 9/1993 |
| WO | 00/15827 A2 | 3/2000 |

OTHER PUBLICATIONS

Wheeler et al., "The biosynthetic pathway of vitamin C in higher plants", Nature (London), May 28, 1998, vol. 393, No. 6683, pp. 365-369.*
French search report completed Jan. 18, 2002—4 pages.
Vitaminology II, Tokyo Kagaku Doujin, Inc.; Nov. 1, 1980 1st edition, pp. 578-581, Tokyo, JP.
Vitaminology Advancement, Vitamin Society of Japan, Feb. 25, 1960, 1st edition, pp. 113-117, Kyoto, JP.

* cited by examiner

*Primary Examiner*—Ruth A Davis
(74) *Attorney, Agent, or Firm*—Buchanan, Ingersoll & Rooney PC

(57) ABSTRACT

The invention concerns a composition for topical application for extemporaneous preparation, comprising ascorbic acid and a suitable support, the ascorbic acid being obtained by bringing at least one ascorbic acid precursor with the exception of its esters into contact with at least one enzyme that is capable of converting said precursor. It also concerns the use of one or more enzymes selected from L-galactono-1, 4-lactone dehydrogenase, L-galactose dehydrogenase, L-sorbosone dehydrogenase, L-gulono-1,4-lactone oxidase and mixtures thereof, or of an extract comprising said enzyme, for the preparation of ascorbic acid for topical use, and a cosmetic method for treating the skin consisting of applying to the skin, either simultaneously or successively, at least one enzyme that can convert an ascorbic acid precursor into ascorbic acid, and at least one ascorbic acid precursor with the exception of its esters.

20 Claims, No Drawings

US 7,182,949 B2

COMPOSITION COMPRISING VITAMIN C PREPARED DURING APPLICATION, USE OF ENZYMES FOR FORMING VITAMIN C FOR TOPICAL USE, AND A COSMETIC TREATMENT METHOD

BACKGROUND OF THE INVENTION

The present invention relates to compositions comprising vitamin C obtained by an enzymatic route, to the use of certain enzymes in the preparation of compositions, in particular cosmetic compositions, and to a cosmetic method involving the application of such compositions to the skin.

Vitamin C, or ascorbic acid, is a very important active ingredient, in particular in cosmetics. It is known to stimulate the growth of connective tissue, in particular collagen, and to reinforce the defenses of cutaneous tissue against external attack. It is also used to remove marks and pigmentations from skin and to encourage healing of injured skin.

A crucial problem with that molecule, however, is its instability, rendering it difficult to formulate into the usual compositions. Further, after applying such compositions, vitamin C rapidly degrades.

Thus, there is a need for compositions, in particular cosmetic or dermatological compositions, comprising ascorbic acid and which can overcome the problem of stability of the active ingredient.

BRIEF SUMMARY OF THE INVENTION

The invention concerns a composition for topical application for extemporaneous preparation comprising ascorbic acid and a suitable support, the ascorbic acid being obtained by bringing at least one ascorbic acid precursor with the exception of ascorbic acid esters into contact with at least one enzyme that is capable of converting said precursor.

DETAILED DESCRIPTION OF THE INVENTION

In accordance with the invention, the vitamin C is generated directly, during or just before its application to the skin, or even after application, i.e., just before its absorption.

This method overcomes problems encountered until now with formulations involving vitamin C.

Further, in certain implementations in which the transformation of precursors by the enzyme is steady, the compositions and the method of the invention can achieve constant and regular liberation at the skin surface; as a result, in vivo bioavailability is better and the compositions are more effective.

Further, the present invention concerns the use of one or more enzymes selected from L-galactono-1,4-lactone dehydrogenase, L-galactose dehydrogenase, L-sorbosone dehydrogenase, L-gulono-1,4-lactone oxidase or mixtures thereof, or an extract comprising said enzyme for the preparation of ascorbic acid for topical use.

Further, the invention concerns a cosmetic treatment for applying a composition as described above and below to the skin. It also concerns a method for cosmetic treatment of the skin consisting of applying to the skin, in a simultaneous or successive manner, at least one enzyme that is capable of converting an ascorbic acid precursor into ascorbic acid, and at least one ascorbic acid precursor, with the exception of its esters.

The term "precursor" as used in the invention means any chemical or biological precursor of ascorbic acid. Clearly, the precursors includes any sugar or substrate that can be transformed into vitamin C by at least one enzymatic route, for example an oxidation step, with the exception of ascorbic acid esters.

Particular examples of such precursors are certain sugars, including L-galactono-1,4-lactone, L-gulono-1,4-lactone, D-glucorono-1,4-lactone, D-glucuronic acid, D-mannose, D-galacturonic acid, D-glucose, D-galactose, L-galactose or mixtures thereof. Preferably, L-galactono-1,4-lactone is used.

The term "enzyme" as used in the invention means any enzyme or mixture of enzymes capable of converting at least one vitamin C precursor into vitamin C, more particularly the above precursors, this or these enzymes more generally being present in one or more of the forms described below.

Particular examples of such enzymes include L-galactono-1,4-lactone dehydrogenase, L-galactose dehydrogenase, L-sorbosone dehydrogenase and L-gulono-1,4-lactone oxidase. Mixtures thereof can also be used. Preferably, L-galactono-1,4-lactone dehydrogenase is used.

In the compositions of the invention, the enzymes used can be in the form of a crude extract, a solution of purified enzyme(s), enzyme(s) immobilised on a matrix, in particular on a sol-gel matrix, in the solid or liquid form, optionally freeze-dried, included in a controlled release device, encapsulated in or included in liposomes or any other form in which the enzyme or enzymes and the substrate are separated from each other prior to bringing them into contact, just before or at the time of their application.

The enzyme can originate from animals, plants or insects or from micro-organisms, particularly from differentiated or undifferentiated cells obtained in vivo or in vitro before or after genetic modification.

The majority of plants can be considered as suitable sources of enzyme(s). Examples that can be cited are *Arabidopsis thaliana, Rosa* sp. and Pea seedlin. An example of a micro-organism that can express suitable enzymes is *Aerobacter* sp.

The extract comprising the enzyme can be an extract prepared from any substance, in particular cells, said substance having been obtained by in vivo culture. The culture of cells in vitro can produce a standardised substance that is available throughout the year, in contrast to in vivo culture.

The term "in vivo culture" means any technique known to the skilled person that can produce an organism (organ) artificially.

In the plant field, the advantage of in vitro culture is, inter alia, that plants are not subjected to seasons but are accessible throughout the year, thus satisfying the quantitative demands of industry, and under perfectly reproducible conditions since culture takes place in perfectly controlled conditions of temperature, pH and culture medium, thus satisfying the industrial quality criteria.

As an example, in accordance with the invention, the extract can be an extract from an organ such as roots, stems, leaves, flowers, petals, fruit, or even cells of the organ, of at least one plant obtained by in vitro culture, or again an extract of dedifferentiated cells.

Preferably, in accordance with the invention, dedifferentiated plant cells are used.

The term "dedifferentiated plant cells" means any plant cell with none of the characteristics of a particular specialisation that can live autonomously and independently of other cells. If necessary, after induction, these dedifferentiated plant cells can undergo any differentiation made possible by their genome.

Depending on the selected culture method, and in particular on the selected culture medium, a single explant can be used to produce dedifferentiated plant cells with different characters ("Plant Propagation by Tissue Culture", George E. F. and Sherrington P. D., 1984, Exegetics Limited).

Further, the source described in International patent application WO-A-98/02830 can be indicated as a source of cloned enzymes.

In the compositions of the invention, ascorbic acid is prepared by bringing at least one enzyme or an extract comprising at least one enzyme into contact with at least one substrate. In a first variation, the enzyme or enzymes and the precursor(s) are introduced into a single composition, preferably prepared just prior to use.

In a second variation, the enzyme or enzymes and then the precursor are packaged so that they are not in contact with each other before use.

As an example, they can be incorporated into two different compositions for mixing at the time of application or for application in succession or separated over time.

These compositions can be disposed in two separate compartments; they can, however, be brought into communication via a common conduit; the compositions are mixed therein and/or may leave it and mix at the same time, before or during application to the skin.

Dual-compartment packaging devices of that type have been described, for example, in French patents FR-A-2 045 559, FR-A-2 105 332, FR-A-2 258 319, FR-A-2 293 375, FR-A-2 586 913 and FR-A-2 643 615.

Further, it is also possible to produce at least one composition in an encapsulated form and/or in the form of microcapsules or microgranules that can be incorporated into a suitable vehicle, for example into the other composition.

The enzyme and/or precursor can be in the encapsulated form or included in liposomes, in the form of microcapsules or microgranules.

The microcapsules or microgranules or liposomes are crushed at the time of application, or at the time the composition is removed from its packaging, by shear or friction on the skin, for example, which allows the enzyme(s) and precursor(s) to mix at the time of application, and produces vitamin C directly on the skin.

The term "suitable support or medium for topical application" means any cosmetically and/or dermatologically acceptable medium, i.e., compatible with the skin and/or hair. These media usually comprise water or a mixture of water and (a) fatty substance(s) or a mixture of fatty substances.

Fatty substances that can be used in the invention that can be cited are mineral oils (vaseline, mineral oil), plant oils and their hydrogenated derivatives, animal oils, synthesised oils, silicone oils (dimethicone, cyclomethicone) and fluorinated oils. Other fatty substances that can be cited are fatty alcohols, fatty acids and waxes.

In particular, the compositions can be in the form of aqueous, alcoholic or hydroalcoholic solutions, hydrophilic or lipophilic gels, microemulsions, water-in-oil emulsions or oil-in-water emulsions or water-in-oil-in-water or oil-in-water-in-oil emulsions with the appearance of a cream or a gel, which may be capable of foaming, in the form of an aerosol, or in the form of vesicular dispersions containing ionic and/or non ionic lipids. These galenical forms are prepared using the usual methods for the fields under consideration.

As is well known, the medium suitable for topical application in accordance with the invention can also contain ancillary substances that are normal in the cosmetics or dermatological industry, such as hydrophilic or lipophilic gelling agents, surfactants, hydrophilic or lipophilic active ingredients, preservatives, antioxidants, solvents, fragrances, fillers, filters and colorants.

The quantities of different constituents of the compositions of the invention are those that are conventionally employed in the fields under consideration.

In the compositions of the invention, the enzyme is present in a quantity of 0.05% to 30% by weight, preferably 0.1% to 10% by weight with respect to the total composition weight. The precursor is present in a quantity of 0.01% to 50% by weight, preferably 0.1% to 10% by weight with respect to the total composition weight.

The composition of the invention can be used in products for the protection, treatment or care of the face, neck, hands or body; it can be used in self-tanning products or hair care products, in particular for scalp care, for example in the form of treatment lotions, creams or gels.

The following examples are given by way of illustration to provide a clearer indication of the invention and do not limit the invention in any way. The quantities indicated are percentages by weight.

EXAMPLES

Example 1

Skin Care Cream

| Oily phase: | |
|---|---|
| Triceteareth-4 phosphate/sodium $C_{14}$–$C_{17}$ alkyl sec sulfonate (Hostacerin CG sold by Hoechst Celanese) (surfactant) | 6% |
| Vaseline | 2% |
| Mineral oil | 4% |
| Dimethicone | 3% |
| Cyclomethicone | 3% |
| Dimethicone polyol (surfactant) | 1% |
| Triclosan (preservative) | 0.1% |
| L-galactono-1,4-lactone | 1% |
| Aqueous phase | |
| Propylene glycol (humectant) | 2% |
| PEG-20 (organoleptic) | 1% |
| L-galactono-1,4-lactone dehydrogenase | 1% |
| Phenoxyethanol (preservative) | 0.4% |
| Water | qsp 100% |

The L-galactono-1,4-lactone dehydrogenase is introduced into the aqueous phase in the encapsulated form, in microcapsules also containing atelocollagen and glycosaminoglycans.

These microcapsules are immersed in the remainder of the constituents after preparing the emulsion.

Example 2

Cream

Oily phase:

| | |
|---|---|
| Triceteareth-4 phosphate/sodium $C_{14}$–$C_{17}$ alkyl sec sulfonate (Hostacerin CG sold by Hoechst Celanese) (surfactant) | 6% |
| Vaseline | 2% |
| Mineral oil | 4% |
| Dimethicone | 3% |
| Cyclomethicone | 3% |
| Dimethicone polyol (surfactant) | 1% |
| Triclosan (preservative) | 0.1% |
| L-gulono-1,4-lactone | 2% |

Aqueous phase

| | | |
|---|---|---|
| Propylene glycol (humectant) | | 2% |
| PEG-20 (organoleptic) | | 1% |
| L-gulono-1,4-lactone dehydrogenase | | 2% |
| Phenoxyethanol (preservative) | | 0.4% |
| Water | qsp | 100% |

The L-gulono-1,4-lactone is introduced into the composition in the form of microspheres also containing atelocollagen and glycosaminoglycans.

These microspheres are immersed in the remainder of the constituents after preparing the emulsion.

Example 3

Treatment Emulsion

A. Emulsion containing precursor:
Oily phase.

| | |
|---|---|
| Steareth-2 (surfactant) | 3% |
| Steareth-21 (surfactant) | 2% |
| PPG-15 stearyl ether (surfactant) | 29.5% |
| L-galactono-1,4-lactone | 0.5% |

Aqueous phase:

| | | |
|---|---|---|
| Phenoxyethanol (preservative) | | 0.5% |
| Water | qsp | 100% |

B. Emulsion containing enzyme:
Oily phase:

| | |
|---|---|
| Steareth-2 (surfactant) | 3% |
| Steareth-21 (surfactant) | 2% |
| PPG-15 stearyl ether (surfactant) | 29.5% |

Aqueous phase:

| | | |
|---|---|---|
| Phenoxyethanol (preservative) | | 0.5% |
| L-galactono-1,4-lactone dehydrogenase | | 1% |
| Water | qsp | 100% |

Emulsions A and B are disposed in two separate compartments and mixed at the time of application to the skin.

Example 4

Self-tanning Cream

A. Emulsion containing dihydroxyacetone ester:
Oily phase:

| | |
|---|---|
| Steareth-2 (surfactant) | 3% |
| Steareth-21 (surfactant) | 2% |
| PPG-15 stearyl ether (surfactant) | 29.5% |
| L-galactose | 10% |

Aqueous phase:

| | | |
|---|---|---|
| Phenoxyethanol (preservative) | | 0.5% |
| Water | qsp | 100% |

B. Emulsion containing lipase:
Oily phase:

| | |
|---|---|
| Steareth-2 (surfactant) | 3% |
| Steareth-21 (surfactant) | 2% |
| PPG-15 stearyl ether (surfactant) | 29.5% |

Aqueous phase:

| | | |
|---|---|---|
| Phenoxyethanol (preservative) | | 0.5% |
| L-galactose dehydrogenase | | 10% |
| Water | qsp | 100% |

The emulsions are disposed in two separate compartments and mixed at the time of application to the skin.

Example 5

Skin Care Cream

Oily phase:

| | |
|---|---|
| Triceteareth-4 phosphate/sodium $C_{14}$–$C_{17}$ alkyl sec sulfonate (Hostacerin CG sold by Hoechst Celanese) (surfactant) | 5% |
| Stearyl alcohol | 1% |
| Vaseline | 2% |
| Mineral oil | 4% |
| Phenyl trimethicone | 4% |
| Cyclomethicone | 4% |
| Dimethicone/dimethiconol (surfactant) | 2% |
| Triclosan (preservative) | 0.1% |
| L-galactono-1,4-lactone | 0.6% |

Aqueous phase

| | | |
|---|---|---|
| Propylene glycol (humectant) | | 2% |
| PEG-20 (organoleptic) | | 1% |
| L-galactono-1,4-lactone dehydrogenase | | 0.5% |
| Phenoxyethanol (preservative) | | 0.2% |
| Chlorphenesin | | 0.2% |
| Polyacrylamide/$C_{13}$–$C_{14}$ isoparaffin/laureth-7 (Sepigel 305 sold by Seppic) (gelling agent) | | 0.6% |
| Water | qsp | 100% |

The L-galactono-1,4-lactone is introduced into the composition in the form of microspheres also containing atelocollagen and sodium chondroitin sulfate.

These microspheres are immersed in the remainder of the constituents after preparing the emulsion.

Example 6

Skin Depigmentation Cream

A. Emulsion containing precursor:
Oily phase:

| | |
|---|---|
| Steareth-2 (surfactant) | 3% |
| Steareth-21 (surfactant) | 2% |
| PPG-15 stearyl ether (surfactant) | 9% |
| Cetyl alcohol | 2% |
| Vaseline | 5% |

-continued

| | | |
|---|---|---|
| Triclosan (preservative) | | 0.2% |
| L-galactono-1,4-lactone | | 1% |
| Aqueous phase: | | |
| Propylene glycol (humectant) | | 4% |
| PEG-20 (organoleptic) | | 5% |
| Phenoxyethanol (preservative) | | 0.5% |
| Water | qsp | 100% |
| B. Emulsion containing enzyme: | | |
| Oily phase: | | |
| Steareth-2 (surfactant) | | 3% |
| Steareth-21 (surfactant) | | 2% |
| PPG-15 stearyl ether (surfactant) | | 9% |
| Cetyl alcohol | | 2% |
| Vaseline | | 5% |
| Triclosan (preservative) | | 0.2% |
| Aqueous phase: | | |
| Propylene glycol (humectant) | | 4% |
| PEG-20 (organoleptic) | | 5% |
| Phenoxyethanol (preservative) | | 0.5% |
| L-galactono-1,4-lactone dehydrogenase | | 1% |
| Water | qsp | 100% |

Emulsions A and B are disposed in two separate compartments and mixed at the time of application to the skin.

The invention claimed is:

1. A composition for topical application comprising at least one ascorbic acid precursor with the exception of ascorbic acid esters, at least one enzyme that converts said precursor to ascorbic acid, and a cosmetically and/or dermatologically acceptable medium, wherein said at least one ascorbic acid precursor is selected from the group consisting of L-galactono-1,4-lactone, L-gulono-1,4-lactone, D-glucorono-1,4-lactone, D-glucoronic acid, D-mannose, D-galacturonic acid, D-glucose, D-galactose, L-galactose, and mixtures thereof, wherein said at least one enzyme is present in a quantity of 0.1% to 10% by weight with respect to the total composition weight, and wherein said at least one ascorbic acid precursor is present in a quantity of 0.1% to 10% by weight with respect to the total composition weight.

2. The composition of claim 1, wherein said at least one enzyme is L-galactono-1,4-lactone dehydrogenase.

3. The composition of claim 1, wherein said at least one enzyme originates from an extract from plants, animals, insects or from micro-organisms.

4. The composition of claim 1, wherein said at least one enzyme and said at least one precursor are packaged in separate compartments.

5. The composition of claim 1, wherein said at least one enzyme and/or said at least one precursor are in an encapsulated form.

6. The composition of claim 1, wherein said at least one enzyme and/or said at least one precursor are in the form of microcapsules or microgranules.

7. The composition of claim 1, wherein said at least one enzyme is in the form of a crude extract, a purified enzyme solution, an enzyme immobilized on a matrix, in the solid or liquid form, in the liquid or solid freeze-dried form, or included in a controlled release device.

8. The composition of claim 7, wherein said matrix is a sol-gel matrix.

9. The composition of claim 1, wherein said at least one enzyme originates from in vivo- or in vitro-obtained differentiated or dedifferentiated cells.

10. A composition for topical application comprising at least one ascorbic acid precursor with the exception of ascorbic acid esters, at least one enzyme that converts said precursor to ascorbic acid, and a cosmetically and/or dermatologically acceptable medium, wherein said at least one ascorbic acid precursor is selected from the group consisting of L-galactono-1,4-lactone, L-gulono-1,4-lactone, D-glucorono-1,4-lactone, D-glucoronic acid, D-mannose, D-galacturonic acid, D-glucose, D-galactose, L-galactose, and mixtures thereof, wherein said at least one enzyme is selected from the group consisting of L-galactono-1,4-lactone dehydrogenase, L-galactose dehydrogenase, L-sorbosone dehydrogenase, L-gulono-1,4-lactone oxidase, and mixtures thereof, wherein said at least one enzyme is present in a quantity of 0.1% to 10% by weight with respect to the total composition weight, and wherein said at least one ascorbic acid precursor is present in a quantity of 0.1% to 10% by weight with respect to the total composition weight.

11. The composition of claim 10, wherein said at least one enzyme and said at least one precursor are packaged in separate compartments.

12. The composition of claim 10, wherein said composition further comprises ascorbic acid.

13. A composition for topical application comprising at least one ascorbic acid precursor with the exception of ascorbic acid esters, at least one enzyme that converts said precursor to ascorbic acid, and a cosmetically and/or dermatologically acceptable medium, wherein said at least one ascorbic acid precursor is selected from the group consisting of L-galactono-1,4-lactone, L-gulono-1,4-lactone, D-glucorono-1,4-lactone, D-glucoronic acid, D-mannose, D-galacturonic acid, D-glucose, D-galactose, L-galactose, and mixtures thereof, wherein said at least one enzyme is present in a quantity of 0.1% to 10% by weight with respect to the total composition weight, wherein said at least one ascorbic acid precursor is present in a quantity of 0.1% to 10% by weight with respect to the total composition, and wherein said at least one enzyme and said at least one precursor are packaged separately.

14. A composition for topical application comprising at least one ascorbic acid precursor with the exception of ascorbic acid esters, at least one enzyme that converts said precursor to ascorbic acid, and a cosmetically and/or dermatologically acceptable medium, wherein said at least one ascorbic acid precursor is selected from the group consisting of L-galactono-1,4-lactone, L-gulono-1,4-lactone, D-glucorono-1,4-lactone, D-glucoronic acid, D-mannose, D-galacturonic acid, D-glucose, D-galactose, L-galactose, and mixtures thereof, wherein said at least one enzyme is selected from the group consisting of L-galactono-1,4-lactone dehydrogenase, L-galactose dehydrogenase, L-sorbosone dehydrogenase, L-gulono-1,4-lactone oxidase, and mixtures thereof, wherein said at least one enzyme is present in a quantity of 0.1% to 10% by weight with respect to the total composition weight, wherein said at least one ascorbic acid precursor is present in a quantity of 0.1% to 10% by weight with respect to the total composition weight, wherein said at least one enzyme and said at least one precursor are packaged separately.

15. A topical composition comprising at least one ascorbic acid precursor, at least one enzyme that converts said precursor to ascorbic acid, and a cosmetically and/or dermatologically acceptable medium, said at least one enzyme and said at least one precursor being separated from each other until the time of application, wherein said at least one ascorbic acid precursor is selected from the group consisting of L-galactono-1,4-lactone, L-gulono-1,4-lactone, D-glucorono-1,4-lactone, D-glucoronic acid, D-mannose, D-galacturonic acid, D-glucose, D-galactose, L-galactose, and mixtures thereof, wherein said at least one enzyme is present in a quantity of 0.1% to 10% by weight with respect to the total composition weight, and wherein said at least one ascorbic acid precursor is present in a quantity of 0.1% to 10% by weight with respect to the total composition weight.

16. A topical composition comprising at least one ascorbic acid precursor, at least one enzyme that converts said precursor to ascorbic acid, and a cosmetically and/or dermatologically acceptable medium, said at least one enzyme and said at least one precursor being separated from each other until the time of application, wherein said at least one ascorbic acid precursor is selected from the group consisting of L-galactono-1,4-lactone, L-gulono-1,4-lactone, D-glucorono-1,4-lactone, D-glucoronic acid, D-mannose, D-galacturonic acid, D-glucose, D-galactose, L-galactose, and mixtures thereof, wherein said at least one enzyme is selected from the group consisting of L-galactono-1,4-lactone dehydrogenase, L-galactose dehydrogenase, L-sorbosone dehydrogenase, L-gulono-1,4-lactone oxidase, and mixtures thereof, wherein said at least one enzyme is present in a quantity of 0.1% to 10% by weight with respect to the total composition weight, and wherein said at least one ascorbic acid precursor is present in a quantity of 0.1 % to 10% by weight with respect to the total composition weight.

17. The composition according to claim 16, wherein said composition further comprises ascorbic acid.

18. A topical composition comprising at least one ascorbic acid precursor, at least one enzyme that converts said precursor to ascorbic acid, and a cosmetically and/or dermatologically acceptable medium wherein said at least one enzyme and/or said at least one precursor is/are in encapsulated form and/or is/are included in liposomes or microcapsules or microgranules so as to separate said at least one enzyme from said at least one precursor until the time of application, wherein said at least one ascorbic acid precursor is selected from the group consisting of L-galactono-1,4-lactone, L-gulono-1,4-lactone, D-glucorono-1,4-lactone, D-glucoronic acid, D-mannose, D-galacturonic acid, D-glucose, D-galactose, L-galactose, and mixtures thereof, wherein said at least one enzyme is present in a quantity of 0.1 % to 10% by weight with respect to the total composition weight, and wherein said at least one ascorbic acid precursor is present in a quantity of 0.1% to 10% by weight with respect to the total composition weight.

19. A topical composition comprising at least one ascorbic acid precursor, at least one enzyme that converts said precursor to ascorbic acid, and a cosmetically and/or dermatologically acceptable medium wherein said at least one enzyme and/or said at least one precursor is/are in encapsulated form and/or is/are included in liposomes or microcapsules or microgranules so as to separate said at least one enzyme from said at least one precursor until the time of application, wherein said at least one ascorbic acid precursor is selected from the group consisting of L-galactono-1,4-lactone, L-gulono-1,4-lactone, D-glucorono-1,4-lactone, D-glucoronic acid, D-mannose, D-galacturonic acid, D-glucose, D-galactose, L-galactose, and mixtures thereof, wherein said at least one enzyme is selected from the group consisting of L-galactono-1,4-lactone dehydrogenase, L-galactose dehydrogenase, L-sorbosone dehydrogenase, L-gulono-1,4-lactone oxidase, and mixtures thereof, wherein said at least one enzyme is present in a quantity of 0.1 % to 10% by weight with respect to the total composition weight, and wherein said at least one ascorbic acid precursor is present in a quantity of 0.1% to 10% by weight with respect to the total composition weight.

20. The composition according to claim 19, wherein said composition further comprises ascorbic acid.

* * * * *